United States Patent
Kozachuk

(10) Patent No.: US 6,191,117 B1
(45) Date of Patent: Feb. 20, 2001

(54) METHODS OF PRODUCING WEIGHT LOSS AND TREATMENT OF OBESITY

(76) Inventor: Walter E. Kozachuk, Kensington, MD (US)

(*) Notice: Under 35 U.S.C. 154(b), the term of this patent shall be extended for 0 days.

(21) Appl. No.: 09/613,692

(22) Filed: Jul. 10, 2000

(51) Int. Cl.$^7$ .......................... A61K 31/70; A61K 31/55; A61K 31/22; A61K 31/19

(52) U.S. Cl. ........................... 514/23; 514/217; 514/551; 514/557

(58) Field of Search .............................. 514/23, 557, 551, 514/217

(56) References Cited

PUBLICATIONS

Faught E, Wilder BJ, Ramsay RE, et al. "Topiramate placebo–controlled dose–ranging trial in refractory partial epilepsy using 600–, 800–, and 1000–mg daily dosages." Neurology 46:1684–1690, 1996.

Privitera M, Fincham R, Penry J, et al. "Topiramate placebo–controlled dose–ranging trial in refractory partial epilepsy using 600–, 800–, and 1000–mg daily dosages." Neurology 46:1678–1683, 1996.

Package insert. "Topamax (topiramate)." Raritan, NJ: Ortho McNeil Pharmaceutical, Dec. 1996.

Matsuo F, Bergen D, Faught, et al. "Placebo–controlled study of the efficacy and safety of lamotrigene in patients with partial seizures." Neurology 43:2284–2291, 1993.

Brodie MJ, Richens A, Yuen AWC, et al. "Lamotrigene/Carbamazepine Monotherapy Trial Group. (No date aun.l) Double–blind comparison of lamotrigene and carbamezepine in newly diagnosed epilepsy." Lancet 345:476–479.

Brodie MJ, Overstall PW, Giorgio L. "Multicentre, double–blind, randomized comparison between lamotrigene and carbamazepine in elderly patients with newly diagnosed epilepsy. The UK Lamotrigene Elderly Study Group." Epilepsy Res. 37:81–87, 1999.

Steiner TJ, Dellaportas CI, Findley LJ, et al. "Lamotrigene monotherapy in newly diagnosed untreated epilepsy: a double–blind comparison with phenytoin." Epilepsia 40:601–607, 1999.

Gilliam F, Vazquez B, Sackellares JC, et al. "An active–control trial of lamotrigene monotherapy for partial seizures." Neurology 51:1018–1025, 1998.

Reunanen M, Dam M, Yuen AW. "A ramdomized open multicentre comparative trial of lamotrigene and carbamazepine as monotherapy in patients with newly diagnosed or recurrent epilepsy." Epilepsy Res. 23:149–155, 1996.

Besag FM, Dulac O, Alving J, et al. "Long–term safety and efficacy of lamotrigene (Lamictal) in pediatric patients with epilepsy." Seizure 6:51–56, 1997.

Sachdeo RC, Reife RA, Lim P, et al. "Topiramate monotherapy for partial seizures." Epilepsia 38:294–300, 1997.

Rosenfeld WE, Sachdeo RC, Faught RE, et al. "Long–term experience with topiramate adjunctive therapy and as monotherapy in patients with partial onset seizures: retrospective survey of open–label treatment." Epilepsia 38 (Suppl 1) 38:S34–S36, 1997.

Biton V. "Preliminary open–label experience with topiramate in primary generalized seizures." Epilepsia 38(Suppl. 1): S42–S44, 1997.

Martin R. Kuzniecky R, Ho S, et al. "Cognitive effects of topiramate, gabapentin, and lamotrigine in healthy young adults." Neurology 52:321–327, 1999.

Bassel Abou–Khalil. "Topiramate in the long–term management of refractory epilepsy." Epilepsia 41 (Suppl 1): S72–S76, 2000.

Stanley BG, Butterfield BS, and RS Grewal. "NMDA receptor coagonist glycine site: evidence for a role in lateral hyptohalamic stimulation of feeding." Am J Physiol. 73(42): R790–F796, 1997.

Bergen DC, Ristanovic K, Waicosky K, et al. "Weight loss in patients taking felbamate." Clinical Neuropharm 18(1): 23–27, 1995.

Inui A. "Transgenic approach to the study of body weight regulation." Pharmacological Reviews. 52(1): 35–61, 2000.

Wolf AM and GA Colditz. "Current estimates of the economic cost of obesity in the United States." Obes. Res. 6:97–106, 1998.

Kaufman DW, JP Kelly, T Anderson et al. "Evaluation of case reports of aplastic anemia among patients treated with falbamate." Epilepsia 38(12): 1265–1269, 1997.

Stanley BG, VL Willet, HW Donias, et al. "The lateral hypothalamus: a primary site mediating excitatory amino acid–elicited eating." Brain Res. 630: 41–49, 1993.

Sorrels TL and E Bostock. "Induction of feeding by 7–chlorokynurenic acid, a strychnine–insensitve glycine binding site antagonist." Brain Research 572: 265–268, 1992.

Stanley BG, VL Willet, HW Donias, et al. "Lateral hypothalamus NMDA receptors and glutamate as physiological mediators of eating and weight control." Am. J. Physiol. 270 (39): R433–R449, 1996.

Meeker RB, RS Greenwood, and JN Hayward. "Glutamate receptors in the rat hypothalamus and pituitary." Endocrinology 134: 621–629, 1994.

Stricker EM, AF Swerdloff, and MJ Zigmond. "Intrahypothalamic injections of kainic acid produce feeding and drinking deficits in rats." Brain Research 158: 470–473, 1978.

(List continued on next page.)

Primary Examiner—Raymond Henley, III
(74) Attorney, Agent, or Firm—Liniak, Berenato, Longacre & White, LLC

(57) ABSTRACT

Methods are disclosed for the acute and chronic treatment of obesity using drugs whose mechanism includes the interaction and antagonism of the kainate/AMPA receptor. Methods are disclosed for employing the drug topiramate (topomax) as monotherapy or in combination therapy with lamotrigene, valproic acid, valproic acid and carbamezepine combination, or felbamate (felbatol).

7 Claims, No Drawings

PUBLICATIONS

Van den Pol A, JP Wuarin, and FE Dudeck. "Glutamate, the dominant excitatory transmitter in neuroendocrine regulation." Science 250:1276–1278, 1990.

Stanley BG, LH Ha, LC Spears and MG Dee. "Lateral hypothalamic injections of glutamate, kainic acid, D,L-a-amino-hydroxy-5-methyl-isoxazole propionic acid or N-methyl-D-aspartic acid elicit intense transient eating in rats." Brain Research 613: 88–95, 1993.

Wirtshafter D and R Trifunovic. "Stimulation of ingestive behaviors following injections of excitatory amino acid antagonists into the median raphe nucleus." Pharmacol. Biochem. Behav. 30: 529–533, 1988.

Kuzniecky R, Hetherington H, Ho S, et al. "Topiramate increases cerebral GABA in healthy humans." Neurology 51: 627–629, 1998.

Li LM, Nashef L., Moriarty J., et al. "Felbamate as add-on therapy." Eur. Neurol. 36:146–148, 1996.

Privitera MD. "Topiramate: a new antipileptic drug." Ann of Pharmacotherapy 31:1164–1173, 1997.

Pellock JM. "Felbamate." Epilepsia 40 (Suppl 5):S57–S62, 1999.

Weiss S, Kemp DE, and L. Bauce. "Kainate evokes the release of endogenous glycine from striatal neurons in primary culture." Neurosci Lett 107:205–210, 1989.

METHODS OF PRODUCING WEIGHT LOSS AND TREATMENT OF OBESITY

FIELD OF THE INVENTION

The present invention relates to pharmaceutical compositions, whose mechanisms of action(s) are at the kainate/AMPA receptor that can be used to treat the medical condition of obesity.

BACKGROUND OF THE INVENTION

Obesity is one of the most common medical disorders, which affects 30–40% of the population of which 10% may be severe and morbid. Complications of obesity include insulin resistance, diabetes mellitus, hypertension, cardiovascular disease, pseudotumor cerebri, hyperlipidemia, sleep apnea, cancer, pulmonary hypertension, cholecystitis, and osteoarthritis. The mortality from obesity is estimated at 300,000 to 400,000 per annum in the United States. Obesity in humans is commonly measured by the BMI (body mass index) which is the weight in kilograms divided by the height in meters squared. The degree of obesity is determined by comparisons against standard deviations above the means for males and females. The exact etiology of obesity is unknown but occurs when energy intake exceeds energy expenditure. The amount and distribution of body fat may have some genetic predisposition and be under some hormonal control. Hypothalamic structures, which have complex interconnections with the limbic system and other brain structures, control appetite. Some neurochemicals known to be involved in appetite control include: leptin, a substance released from adipose tissue, GLP-1 (glucagon-like peptidel) which promotes satiety, and neuropeptide-Y, a potent stimulator of appetite.

SUMMARY OF THE INVENTION

The present invention proposes a theory of obesity in which dysfunction of the AMPA/kainate and/or NMDA is a contributing etiology. Administration of drugs whose mechanism or action is antagonism of the AMPA/kainate receptor, with or without the combination of glycine-site antagonists, is proposed as a treatment for obesity.

DETAILED DESCRIPTION OF CERTAIN PREFERRED EMBODIMENTS

Excitatory amino acids are divided into NMDA and non-NMDA [kainate (KA) and AMPA] subtypes. NMDA, KA, and AMPA receptors are concentrated in the lateral hypothalamus, hippocampus and cerebral cortex.

The NMDA receptor complex is located on the neuronal cell surface and is comprised of multiple binding sites as well as an ion-channel with several internal binding sites. Unique features of the NMDA receptor include strychnine insensitivity, blockade by physiological concentrations of Mg++, a high permeability to Ca++, and coactivation by glycine. However, the interaction of the NMDA, KA, and AMPA receptors are not completely understood. The release of endogenous glycine, which acts at the glycine site of the NMDA receptor, from the striatal neurons in primary culture, has been reported to be regulated principally by excitatory amino acids at the kainate receptor system.

High densities of NMDA receptors located in the ventromedial (VMH), medial (MH) and lateral hypothalamus (LH) suggest a prominent role in neuroendocrine and autonomic regulation. The NMDA receptor appears to play a significant physiological role in natural eating and body weight regulation. Studies suggest that NMDA, AMPA, and KA receptor subtypes exist on LH neurons and their activation triggers intense eating. In animals, NMDA receptor blockade of the LH caused marked body weight loss and reduced eating at the onset of the circadian feeding period and after fasting.

Glutamate and its agonists act within the LH to elicit eating and thus participate of the LH in the regulation of eating behavior. LH injections of either glutamate, KA, AMPA, and NMDA elicit a strong dose-dependent eating response. Lateral hypothalamic NMDA blockade reduced the eating response to NMDA and suppressed both deprivation-induced eating and nocturnal eating. These results suggest that endogenous LH glutamate and the NMDA receptor are both involved in the regulation of natural eating, circadian factors, and eating behavior. Thus, NMDA receptors in the LH may participate in the long-term regulation of food intake and body weight control. There is evidence that they also provide mechanisms to account for the experience-dependent plasticity and modulation by motivational state exhibited by some feeding-related LH neurons.

Feeding and drinking are impaired in rats previously given intrahypothalamic injections of kainic acid, a neurotoxic agent that destroys neurons with cell bodies in the lateral hypothalamus but spares fibers of passage. Kainic acid (KA), D,L-α-amino-3-hydroxy-5-methyl-isoxazole proprionic acid (AMPA) or N-methyl-D-aspartate (NMDA) injected into the lateral hypothalamus each elicited eating in a dose-dependent fashion. The effectiveness of all three of these agonists suggests that these receptor subtypes are each expressed by some LH neurons that regulate eating. There is substantial hypothalamic NMDA and AMPA receptor subtype gene expression and evidence that both NMDA and non-NMDA receptors are critical for eating behavior and weight control. NMDA receptors may mediate neural plasticity and learning, which may contribute to the pathophysiology of obesity. Thus, glutamate and several of its agonists can act within the LH to elicit eating, suggest that glutamate and several of its receptor subtypes may participate in LH regulation of eating behavior.

Glutamate and its agonists are relatively ineffective in the PVN (paraventricular nucleus) and PFH (perifornical hypothalamus). These hypothalamic sites are involved in the regulation of eating behavior and in mediating some of glutamate's other physiological effects. Specifically, the PVN has been identified as a primary locus for the feeding-stimulatory effects of norepinephrine, galanin and γ-aminobutyric acid, while the PFH has been identified as a primary site for the feeding-stimulatory effects of neuropeptide Y and the feeding-suppressive effects of dopamine and epinephrine. Moreover, both sites appear to express functional glutamate-sensitive receptors, since PVN or PHF injections of glutamate can produce autonomic and endocrine effects. That glutamate acts primarily in the LH, and neuropeptide y in the PFH to elicit eating, suggests that these adjacent sites are functionally distinct with respect to eating. Some LH eating-regulatory neurons express multiple excitatory amino acid receptors, possibly including the kainate, AMPA, and NMDA subtypes. Autoradiogrpahic studies reveal low levels of hypothalamic NMDA and AMPA binding, and only moderate levels of kainate binding. In contrast, there is evidence for substantial hypothalamic NMDA and AMPA receptor mediation of other physiologic effects in the hypothalamus.

In the lateral hypothalamus, glutamate may act as a physiological mediator of feeding behavior since injection of glutamate elicited eating in satiated rats. The 10 application of AMPA, KA, and NMDA to the lateral hypothalamus was able to trigger intense eating. The NMDA receptor gates Ca++, is both ligand and voltage sensitive, and is regulated by multiple modulatory sites. These mechanisms may account for some of the experience-dependent plasticity and modulation by motivational state exhibited by some feeding-related LH neurons.

To elucidate the role of the glycine binding site on the NMDA receptor in feeding control, a glycine site-antagonist injected into the LH of satiated rats blocked the stimulatory eating response of NMDA. Glycine-site antagonism also blocked the stimulatory feeding effects of KA and AMPA in a dose-dependent manner. In addition, bilateral LH injection of a glycine site antagonist also suppressed eating produced by fasting. These findings suggest an important role of the NMDA receptor glycine site in LH regulation of eating behavior.

Thus the glycine site antagonist 7-chlorokynurenic acid (7-CK) was injected into the lateral hypothalamus (LH) of satiated rats before LH injection of NMDA. 7-CK blocked the 6- to 10-gram eating response elicited by NMDA. LH pretreatment with glycine, suggesting a specific action at the glycine site reversed this block. In contrast to the suppression produced by high doses, 7-CK at 0.1 nmol enhanced NMDA-elicited eating. In addition, 7-CK at a dose of 0.1 nmol suppressed feeding elicited by KA or AMPA, but at 10 nmol it suppressed eating elicited by AMPA while enhancing eating elicited by KA. Finally, bilateral LH injection of 7-CK effectively suppressed eating produced by fasting.

Specifically, the 0.1-nmol dose of 7-CK that enhanced NMDA-elicited eating suppressed KA-elicited eating, and the 10-nmol dose that blocked NMDA-elicited eating markedly enhanced the KA-elicited response. 7-CK had a significant effect on eating elicited by AMPA, with both doses of 7-CK suppressed eating, with the 0.1-nmol dose virtually blocking it.

In a further study, D-APS reduced by 72–90% the 10-gram eating response elicited by NMDA without affecting the quantitatively similar eating responses elicited by kainic acid or AMPA. This treatment also suppressed deprivation-induced eating responses by as much as 61% and nocturnal eating by as much as 40%. The injection of D-AP5 into the LH bilaterally for 8 n days caused a 65% reduction in daily food intake and body weight loss of up to 13 grams/day. These findings suggested those endogenous LH glutamate acts to regulate natural eating and body weight and that NMDA receptors participate in these functions. Endogenous glutamate and NMDA receptors are important modulators of natural eating, specifically that generated by nutrient deprivation and circadian factors. Many LH neurons are also sensitive to food-related taste, olfactory, auditory, and visual inputs and NMDA receptors may participate in mediating the effects on eating behavior of some of these inputs.

Conversely, other studies have reported that the strychnine-insensitive glycine-binding site antagonist, 7-chlorokyneurenic acid (7CK) dose-dependently increased food intake in rats when administered into the intracerebral ventricles or paraventricular nucleus of the hypothalamus. In addition, D-serine, a strychnine-insensitive glycine-binding site agonist, dose-dependently antagonized 7CK induced feeding. Other brain structures may also be involved in appetite control since median raphe injection of excitatory amino acid antagonists elicited eating.

I believe that one etiology of obesity is dysfunction of the NMDA/AMPA/kainate receptors. This may include abnormal quantities of receptors, abnormal function of receptors, or abnormal interaction of these receptors.

Topomax

Topiramate (topomax) is a sulfamate-substituted monosaccharide, which is approved as adjunctive therapy in patients with partial onset seizures, or primary generalized tonic-clonic seizures. Topiramate (TPM) has the molecular formula $C_{12}H_{21}NO_8S$ and a molecular weight of 339.37 and is designated chemically as 2,3:4,5-DI-O-isolpropylidene-B-D-fructopyranose sulfamate. Tablets are available as 25 mg, 100 mg, and 200 mg round tablets for oral administration.

The known mechanisms of action of TPM include: a voltage-sensitive sodium channel blocking action, potentiation of the effects of GABA, and antagonizing the kainate/AMPA ($\alpha$-amino-3-hydroxy-5-methylisoxazole-4-proprionic acid; non-NMDA) subtype of excitatory acid (glutamate) receptor. Using magnetic resonance spectroscopy, TPM was found to acutely increase brain levels of cerebral GABA within three hours of oral administration. TPM has no effect on the activity of N-methyl-D-aspartate (NMDA) at the NMDA receptor subtype. The effects of TPM are concentration-dependent within the range of 1 $\mu$M to 200 $\mu$M. TPM also inhibits some isoenzymes of carbonic anhydrase (CA-II and CA-IV) but this pharmacological effect is weaker than that of acetozolamide, a known carbonic anhydrase inhibitor, and is currently not thought to be a major factor in the antiepileptic activity of TPM.

Absorption of TPM is rapid, with time to peak (TTP) plasma concentrations occurring about 2 hours following a 400 mg dose. The relative bioavailability of TPM from the tablet formation is not affected by food. The pharmacokinetics of TPM is linear with dose proportional increases in plasma concentration over the dose range of 200 to 800 mg/day. The mean plasma concentration half-life is 21 hours after either single or multiple doses. Steady state is reached in about 4 days in patients with normal renal function. TPM is 13–17% bound to human plasma proteins over the concentration range of 1–250 $\mu$g/ml. The mean TTP plasma concentration was between 1.4 and 4.3 hours with TPM doses ranging from 100 to 1200 mg. Absorption is nearly complete, with 81–95% of a 100-mg dose recovered in urine. TPM is a lipophilic substance with a volume of distribution of 0.80-0.55 L/kg and plasma protein binding is minimal, approximately 15%. Elimination of TPM (and its metabolites) is predominantly renal, with 50–80% of a dose excreted as unchanged TPM. TPM is not extensively metabolized and is primarily eliminated unchanged in the urine (approximately 70% of an administered dose). Six metabolites have been identified in humans, none of which constitutes more than 5% of an administered dose. The metabolites are formed via hydroxylation, hydrolysis, and glucuronidation. There is evidence of renal tubular reabsorption of TPM. In humans, plasma clearance (CL/F) is approximately 20 to 30 mL/min following oral administration.

In patients with normal renal function, the elimination half-life for TPM is 20–30 hours, allowing steady-state plasma concentrations to be achieved in 4–8 days. In patients with moderate or severe renal impairment, TPM plasma levels are increased as plasma and renal clearances are reduced. In patients with hepatic impairment, TPM plasma concentrations increased by 29%. The clearance of TPM was reduced by 42% in moderate renal impairment (creatinine clearance 30–69 mL/min/1.73 $m^2$) and by 54% in severe renal impairment (creatinine clearance <30 mL/min/1.73 $m^2$) compared to normal renal function subjects (creatinine clearance >30 mL/min/1.73 m$^2$). In hepatically impaired subjects, the clearance of TPM may be decreased. However, the mechanism(s) underlying the decrease is not well understood.

The recommended titration of TPM therapy is an initiation at 50 mg/day with weekly increases of 50 mg/day. The current recommended total daily dose of TPM as adjunctive epilepsy therapy is 400 mg in two divided doses. In a monotherapy study, adult patients were randomized to a treatment dosage of 1000 mg/day administered twice daily and were maintained at this dose for 112 days. In some studies, doses of 1600 mg/day and long-term administration (>60 months) have been achieved, with mean doses of TPM averaging 700 mg/day. A therapeutic plasma concentration range has not been established for TPM and specific plasma concentrations were not correlated with the occurrence of adverse events. Therefore, clinicians have been advised to use clinical effect as a guide for titrating TPM.

Common adverse events of TPM at dosages of 200 to 400 mg/day in controlled trials in adults with partial onset seizures, primarily generalized tonic-clonic seizures, or Lennox-Gastaut syndrome were: somnolence, dizziness, ataxia, speech disorders and related speech problems, psychomotor slowing, abnormal vision, difficulty with memory, paresthesia and diplopia. These adverse events occurred at a greater frequency in TPM-treated patients and did not appear to be dose-related.

Conversely, the most common dose-related adverse events at dosages of 200 to 1,000 mg/day were: fatigue, nervousness, difficulty with concentration or attention, confusion, depression, anorexia, language problems, anxiety, mood problems, and weight decrease. The most common dose-related adverse events with dosages of 200–1000 mg/day were fatigue, nervousness, difficulty with concentration or attention, confusion, and depression. These adverse events have been attributed to the rapid rate of dose titration of 200 mg/day. However, the majority of these adverse events abated after 4 months of treatment. In a study of the acute and steady-state cognitive effects of TPM on young healthy adults, statistically significant declines on measures of attention and word fluency at both acute doses and at both 2- and 4- week test periods.

In clinical trials on seizure patients, weight loss averaged 2–8 kg (2–8% decline from baseline weight). Patients experiencing weight loss were more likely to report anorexia or loss of appetite. Paradoxically, weight loss tended to be higher in patients also being treated with valproate, or valproate with carbamazepine. Both of these drugs have been associated with weight gain when used as monotherapy. Weight loss generally peaked after 12–15 months of therapy, with body weight gradually returning toward pre-topiramate levels after prolonged therapy. As adjunctive therapy in adult seizure patients, weight decrease occurred more frequently: control 3%, 200–400 mg/day of TPM 9%, and 600–1,000 mg/day of TPM 13%. In a monotherapy study in epilepsy patients, anorexia occurred at 100 mg (13%) and 1000 mg (42%) doses. In another study in epileptic patients, weight loss occurred in 5/12 patients (12–42 pounds) while weight increase was observed in 2/12 patients (12–25 pounds). In a long-term study of epileptic patients receiving TPM, 26% of patients treated for up to 2.2 years experienced weight loss.

Central nervous system adverse events are associated with the use of TPM. These included psychomotor slowing, difficulty with concentration, and speech or language problems, in particular, word-finding difficulty and somnolence and/or fatigue. Additional nonspecific CNS effects occasionally observed with TPM as add-on therapy include dizziness or imbalance, confusion, memory problems, and exacerbation of mood disturbances (i.e., irritability and depression). Reports of psychomotor slowing, speech and language problems, and difficulty with concentration and attention were common in adults. Somnolence and fatigue were the most frequently adverse event during the clinical trials, which were generally mild to moderate and occurred early in therapy. While the incidence of somnolence does not appear to be dose-related, that of fatigue increases at dosages above 400 mg/day.

Adverse events include renal calculi (kidney stones) which occurred in 1.5% of adults, an incidence about 2–4 times that expected in a similar, untreated population. This may be due to the fact that TPM is a weak carbonic anhydrase inhibitor and promote stone formation by reducing urinary citrate excretion and by increasing urinary pH. The concomitant use of TPM in patients on a ketogenic diet may create a physiological environment that increases the risk of kidney stone formation, and is therefore not recommended.

In controlled clinical trials, 11% of patients receiving 200 to 400 mg/day as adjunctive therapy discontinued due to adverse events and increased at dosages above 400 mg/day. Adverse events associated with discontinuing therapy included somnolence, dizziness, anxiety, difficulty with concentration or attention, fatigue, and paresthesia and increased at dosages above 400 mg/day. In post-marketing data, reported adverse experiences included hepatic failure, hepatitis, pancreatitis, and renal tubular acidosis.

The efficacy of TPM in non-epileptic patients with obesity is unknown. There is currently no published study on the effects of TPM in patients with obesity. In addition, the possibility exists that cognitive impairment in patients receiving TPM may prevent adequate dose administration to produce weight loss in obese patients.

Lamotrigene

Lamotrigene (LTG) is an anticonvulsant whose mechanism of action is blocking the sodium channel. A common adverse event is anorexia and nausea (6–15%) which occurred at both doses of 100 mg and 200 mg, adjunctive therapy, and monotherapy. LTG had no significant effect on body weight when administered for 12 months or up to 144 weeks. The combination of LTG and TPM in obese patients may be additive in their effects by producing both anorexia and possibly weight loss.

Felbamate

Felbamate (FBM) was approved as an anti-epileptic drug in 1993. FBM functions as a glycine site NMDA antagonist but other mechanisms of action reported include interaction at the kainate/AMPA receptor, modulation of the Na++ channel conductance, facilitation of the GABA receptor, an interaction at the L-type calcium channels.

In clinical studies prior to FDA approval, FBM was evaluated as add-on therapy (in combination with other standard epileptic drugs) in patients with Lennox-Gestalt Syndrome (intractable seizures with mental retardation). Several mild cases of thrombocytopenia and neutropenia were reported but these were reversible and common adverse events of the other concomitant antiepileptic drugs. Prior to drug approval, there were no reported cases of aplastic anemia or hepatic dysfunction, when standard drug monitoring parameters were performed. Drug interactions included elevation of dilantin, depakote, phenobarbitol levels and the toxic epoxide metabolite of tegretol. In 1994, there were reports of FBM causing aplastic anemia and hepatic failure. As a result, the FDA and manufacturer sent a letter to all physicians in August 1994 requiring the withdrawal of FBM from patients whom were considered at risk for aplastic anemia. Warnings were added to the prescribing information and both hematological and hepatic indices were required every two weeks. In a study on epileptic patients published after the FDA warning, ill patients with refractory epilepsy were treated with adjunctive FBM therapy. No cases of aplastic anemia or hepatic dysfunction were observed when serum levels of all anticonvulsant drugs were monitored. Recent analysis has suggested that only several cases of aplastic anemia could be possibly be attributed to FBM monotherapy. In the absence of any adverse event, recent analysis has suggested that FBM, even in adjunctive therapy, is relatively safe after usage for at least one year.

FBM has been known to induce anorexia and weight loss in patients treated for epilepsy. In a study of FBM as add-on therapy in partial epilepsy in non-obese patients, weight loss was transient and returned to baseline after twenty weeks. Weight loss of 5% was reported in non-obese patients of FBM monotherapy. The weight loss in these patients was attributed to nausea and vomiting as well as the withdrawal of other medications whose side effects were weight gain. We postulate that weight loss from FBM is most likely due to NMDA receptor and non-NMDA modulation of the various hypothalamic structures and receptors involved in appetite control. The mechanisms of action and anecdotal reports of weight loss with monotherapy suggest that FBM is a potentially excellent therapeutic agent in subjects with obesity. In a study of cognitive effects of FBM and tegretol in epileptic patients, FBM was found to increase both cognition and fine motor function. In patients who suffer cognitive decline while receiving TPM, adjunctive FBM may be able to reverse these abnormal cognitive adverse effects.

I claim:

1. A method for treating a human suffering from obesity, comprising the steps of:

administering to the human a compound whose mechanism of action includes antagonism of the kainite and/or AMPA receptor.

2. The method of claim 1, further comprising administering to said human topiramate monotherapy at dose ranges of 1 mg to 5000 mg per day.

3. The method of claim 1, further comprising administering to said human topiramate monotherapy at dose ranges more preferably from 400–2000 per day.

4. The method of claim 1, further comprising administering to said human topiramate in combination with lamotrigene.

5. The method of claim 1, further comprising administering to said human topiramate in combination with valproic acid.

6. The method of claim 1, further comprising administering to said human topiramate in combination with both valproic acid and carbamezepine.

7. The method of claim 1, further comprising administering to said human topiramate in combination with felbamate.

* * * * *